United States Patent [19]

Ozaki et al.

[11] Patent Number: 4,874,698
[45] Date of Patent: Oct. 17, 1989

[54] PROCESS FOR PRODUCING TRYPTOPHAN

[75] Inventors: Akio Ozaki; Ryoichi Katsumata, both of Tokyo; Tetsuo Oka, Yokohama, all of Japan

[73] Assignee: Kyowa Hakko Kogyo Co., Ltd., Tokyo, Japan

[21] Appl. No.: 73,888

[22] Filed: Jul. 16, 1987

Related U.S. Application Data

[63] Continuation of Ser. No. 580,815, Feb. 16, 1984, abandoned.

[30] Foreign Application Priority Data

Feb. 17, 1983 [JP] Japan ................................. 58-25398

[51] Int. Cl.$^4$ .................... C12P 13/22; C12N 1/20; C12N 15/00; C12R 1/13 C12R 1/15
[52] U.S. Cl. .................. 435/108; 435/252.32; 435/320; 435/840; 435/843; 935/60; 935/72
[58] Field of Search ............... 435/108, 172.3, 252.32, 435/320, 840, 843; 935/60, 72

[56] References Cited

U.S. PATENT DOCUMENTS

| | | | |
|---|---|---|---|
| 4,371,614 | 2/1983 | Anderson et al. | 935/16 X |
| 4,495,283 | 1/1985 | Araki | 435/107 |
| 4,601,983 | 7/1986 | Nakamori | 435/115 |

FOREIGN PATENT DOCUMENTS

| | | | |
|---|---|---|---|
| 0553843 | of 0000 | Australia | 435/115 |
| 0556761 | 6/1983 | Australia | 435/172.3 |
| 0058889 | 9/1982 | European Pat. Off. | 935/29 |
| 0063763 | 11/1982 | European Pat. Off. | 435/843 |
| 0066129 | 12/1982 | European Pat. Off. | 435/172.3 |
| 0071023 | 2/1983 | European Pat. Off. | 435/172.3 |
| 0082485 | 6/1983 | European Pat. Off. | 435/172.3 |
| 0088166 | 9/1983 | European Pat. Off. | 435/172.3 |
| 0093611 | 11/1983 | European Pat. Off. | 435/172.3 |
| 0131171 | 1/1985 | European Pat. Off. | 435/172.3 |
| 0136359 | 4/1985 | European Pat. Off. | 935/29 |
| 2076853 | 12/1981 | United Kingdom | 435/172.3 |

OTHER PUBLICATIONS

Aiba, S. et al, *Applied & Environmental Microbiology*, vol. 43 (No. 2), pp. 289–297 (1982).

*Primary Examiner*—Jayme A. Huleatt
*Attorney, Agent, or Firm*—Fitzpatrick, Cella, Harper & Scinto

[57] ABSTRACT

Disclosed is a process for producing tryptophan by transforming a host microorganism belonging to the genus Corynebacterium or Brevibacterium with a recombinant DNA of a DNA fragment containing a gene involved in the biosynthesis of tryptophan and a vector DNA, culturing the transformant in a nutrient medium, accumulating tryptophan in the culture medium and recovering tryptophan therefrom.

8 Claims, No Drawings

PROCESS FOR PRODUCING TRYPTOPHAN

This application is a continuation of application Ser. No. 580,815 filed Feb. 16, 1984, now abandoned.

BACKGROUND OF THE INVENTION

For the direct production of tryptophan by fermentation, methods using mutant strains requiring nutrients and/or resistant to tryptophan analogs of the bacteria belonging to the genus Corynebacterium, Brevibacterium, and the like are known (Japanese Patent Publication Nos. 4505/72 and 19037/76).

No example of expressing a desired gene in a host microorganism belonging to the genus Corynebacterium or Brevibacterium by introducing a recombinant DNA containing such desired gene and vector, one of which is foreign to a host microorganism, into such host microorganism has been reported. In the recombinant DNA technology using a microorganism belonging to the genus Corynebacterium or Brevibacterium as a host, it is necessary to construct vectors autonomously replicable in these microorganisms, having selectable markers and useful for cloning of desired genes, and to establish an efficient transformation system. Further, methods to overcome various barriers against the expression of foreign recombinant DNA will be necessary.

The present inventors have constructed plasmid vectors autonomously replicable in a microorganism belonging to the genus Corynebacterium or Brevibacterium and having selectable markers and adequate cloning sites and have developed a highly efficient transformation system (Japanese Published Unexampined Patent Application Nos. 183799/82, 186492/82, 186489/82 and 105999/83). Further, the present inventors have found that the plasmid vectors are useful for expressing a foreign gene in a host micoorganism and increasing the productivity of amino acids by ligating a DNA fragment containing a foreign gene involved in the biosynthesis of amino acids such as glutamic acid and lysine to the plasmid vectors according to the procedures in recombinant DNA technology (U.S. Pat. No. 4,237,224 and Methods in Enzymology 68, Recombinant DNA, edited by Ray Wu, Academic Press 1979) and transforming Corynebacterium glutamicum L-22 or its derivatives using the transformation methods described in Japanese Published Unexamined Patent Application No. 126789/83.

Furthermore, the present inventors have found that a microorganism prepared by the same method has acquired an increased productivity of tryptophan.

SUMMARY OF THE INVENTION

This invention relates to a process for producing tryptophan by a novel expression method of a gene. More specifically, the present invention is a process for producing tryptophan by transforming a host microorganism belonging to the genus Corynebacterium or Brevibacterium with a recombinant DNA of a DNA fragment containing a gene involved in the biosynthesis of tryptophan and a vector DNA, culturing the transformant in a nutrient medium, accumulating tryptophan in the culture medium and recovering tryptophan therefrom.

DESCRIPTION OF THE INVENTION

The present invention provides a process for producing tryptophan by cultivating in a medium a transformant which is obtained by transforming a microorganism belonging to the genus Corynebacterium or Brevibacterium with a recombinant DNA of a DNA fragment containing a gene involved in the biosynthesis of tryptophan and a vector DNA.

As the DNA fragment containing the gene used in the present invention, the DNA fragment containing a gene involved in the biosynthesis of tryptophan derived from eukaryotes, prokaryotes, viruses, bacteriophages or plasmids is used. As the gene derived from prokaryotes, the gene derived from a bacterium belonging to the genus Escherichia, Cornyebacterium, Brevibacterium, Bacillus, Staphylococcus or Serratia and responsile for the biosynthesis of tryptophan or the metabolism relating to the biosynthesis is preferably used.

The vector used in the present invention should autonomously replicate in cells of the host microorganism. Preferably, plasmids isolated from microorganisms belonging to the genus Corynebacterium by the present inventors or derivatives thereof such as pCG1 (Japanese Published Unexamined Patent Application No. 134500/82), pCG2 (Japanese Published Unexamined Patent Application No. 35197/83), pCG4 (Japanese Published Unexemined Patent Application No. 183799/82), pCE52, pCE53, pCE54, pCG11 and pCB101 are used.

Microorganisms carrying the following plasmids have been deposited with the Fermentation Research Institute, Agency of Industrial Science and Technology, Ibaraki, Japan and the Americal Type Culture Collection, Rockville, Md., U.S.A. under the following accession numbers.

| Plasmid | FERM P- | ATCC |
|---|---|---|
| pCG1 | 5865 | 31808 |
| pCG2 | 5954 | 31832 |
| pCG4 | 5939 | 31830 |
| pCE54 | — | 39019 |
| pCG11 | — | 39022 |
| pCB101 | — | 39020 |

Of the foregong plasmids, pCE52, pCE53 are most preferred. Plasmid pCE52 and pCE53 can be prepared as follows. Plasmid pCG1 is isolated from the cells of Corynebacterium glutamicum 225-57 (FERM P-5865, ATCC 31808) by the method described in the above application and plasmid pGA22 is isolated from the cultured cells of Escherichia coli by the method of An, G. et al., J. Bacteriol. 140,400(1979). pCG1 with a unique BglII site is linearized with restriction enzyme BglII and pGA22 with two BamHI sites are partially digested with BamHI. The cohesive ends of both plasmids are annealed and ligated with T4 phage DNA ligase (T4 ligase) to make a composite molecule. Selection of the recombinant plasmids from the ligation mixture is carried out by isolating transformants of the genus Corynebacterium or Brevibacterium on the basis of drug-resistances derived from pGA22 and then analyzing the plasmids in the transformants.

Transformation with the ligated DNA mixture is carried out using protoplasts of the genus Corynebacterium or Brevibacterium, and the method described in Japanese Published Unexamined Patent Application Nos. 186492/82 and 186489/82.

Among the genes responsible for drug resistance derived from pGA22, those except for the resistance gene which is insertionally inactivated are used for selection. Transformants are recovered as a colony regenerated on a hypertonic agar medium containing 0.4–1.6 μg/ml tetracycline (Tc), 2.5–5 μg/ml chloramphenicol (Cm) or 100–800 μg/ml kanamycin (Km) which does not allow the reversion to normal cells of the protoplasts which are not treated with the ligation mixture. Alternatively, transformants are regenerated unselectively on a regeneration medium, and the resultant cells are scraped and resuspended, followed by the isolation of those cells grown on an agar medium containing a drug in a concentration wherein the recipient normal cells can not grow, that is generally 0.5–4 μg/ml Tc, 2–15 μg/ml Cm or 2–25 μg/ml Km. Some of the transformants resistant to tetracycline ($Tc^R$), chloramphenicol ($Cm^R$) or kanamycin ($Km^R$) are simultaneously endowed with other drug-resistances derived from plasmid pGA22.

Plasmid DNAs in these transformants can be isolated from cultured cells of the transformants and purified according to the methods described in Japanese Published Unexamined Patent Application Nos. 134500/82 and 186489/82. The structures of the DNAs can be determined by digesting them with various restriction endonucleases and analyzing the DNA fragments by agarose gel electrophoresis. The plasmids isolated from the transformants are named pCE52 and pCE53.

pCE52 and pCE53 have a molecular weight of about 10.9 Kb and cleavage sites for EcoRI, SalI, SmaI and XhoI. While pCE52 gives the phenotypes of $Cm^R$ and $Km^R$, pCE53 gives $Tc^R$, $Cm^R$ and $Km^R$ phenotypes. Since the cleavage site for XhoI is present in the $Km^R$ gene, selection by insertional inactivation (prevention of the expression of a gene by the insertion of a DNA fragment into the gene) is possible. Recovery of plasmids from the strains is carried out according to the methods described in Japanese Published Unexamined Patent Application Nos. 134500/82, 183799/82 and 35197/83.

Preparation of a recombinant DNA of a vector DNA with a DNA fragment containing a gene is carried out by conventional in vitro recombinant DNA technology, e.g. cleavage and ligation of a donor DNA containing a desired gene to a vector DNA (refer to Japanese Published Unexamined Patent Application No. 126789/83, U.S. Pat. No. 4,237,224).

The ligase reaction gives recombinants containing genes other than the desired gene. The desired recombinant DNA can be obtained by directly transforming a microorganism of the genus Corynebacterium or Brevibacterium with the ligated DNA mixture, selecting the transformants having the phenotype derived from the desired gene and isolating the desired recombinant DNA from the cultured cells of the transformants. Instead of cloning the desired gene directly in a microorganism of the genus Corynebacterium or Brevibacterium, the desired gene can be cloned by using another host-vector system such as *Escherichia coli*. Then, it is recloned in vitro into a vector of the genus Corynebacterium or Brevibacterium to transform these microorganisms and transformants containing the desired recombinant plasmid are selected as mentioned above.

The following references are helpful for the construction of recombinant DNA:

S. N. Cohen, et al., U.S. Pat. No. 4,237,224;

Idenshi Sosa Jikkenho, edited by Yasuyuki Takagi, printed by Kodansha Scientific (1980);

Methods in Enzymology 68, Recombinant DNA edited by Ray Wu, Academic Press, 1979

Japanese Published Unexamined Patent Application No. 126789/83.

Microorganisms belonging to the genus Corynebacterium or Brevibacterium and which are competent for incorporating DNAs may be used as the host microorganisms in the present invention. Preferably, microorganisms sensitive to lysozyme described in Japanese Published Unexamined Patent Application Nos. 186489/82 and 56678/83 are used. The following are examples of a suitable host microorganism.

|  | Accession Number | |
| --- | --- | --- |
|  | FERM P- | ATCC |
| Corynebacterium glutamicum L-15 | 5946 | 31834 |
| Corynebacterium glutamicum LA-105 | BP-1238 |  |
| Corynebacterium herculis L-103 | 5947 | 31866 |
| Brevibacterium divaricatum L-204 | 5948 | 31867 |
| Brevibacterium lactofermentum L-312 | 5949 | 31868 |

Transformation of the host microorganisms with recombinant DNAs is carried out by the following steps:

(1) Preparation of protoplasts of host cells;

(2) Transformation of the protoplasts with a recombinant DNA;

(3) Regeneration of the protoplasts to normal cells and selection of a transformant;

These steps are described in detail below.

1. Preparation of protoplasts of host cells

The preparation of protoplasts is carried out by culturing a microorganism under conditions which render it sensitive to lysozyme, a lytic enzyme, and treating the cultured cells with lysozyme in a hypertonic solution to remove the cell wall. In order to render microbial cells sensitive to lysozyme, reagents inhibiting the synthesis of bacterial cell walls are used. For example, microbial cells sensitive to lysozyme are obtained by adding, during the logarithmic growth phase, an amount of penicillin which does not inhibit or sub-inhibits the growth and then continuing culturing for several generations.

For culturing, any medium wherein the microorganism can grow may be used. For example, a nutrient medium NB (pH 7.2) consisting of 20 g/l powdered bouillon and 5 g/l yeast extract with a semi-synthetic medium SSM (pH 7.2) consisting of 10 g/l glucose, 4 g/l NH$_4$Cl, 2 g/l urea, 1 g/l yeast extract, 1 g/l KH$_2$PO$_4$, 3 g/l K$_2$HPO$_4$, 0.4 g/l MgCl$_2$.6H$_2$O, 10 mg/l FeSO$_4$.7H$_2$O, 0.2 mg/l MnSO$_4$.(4–6)H$_2$O, 0.9 mg/l ZnSO$_4$.7H$_2$O, 0.4 mg/l CuSO$_4$.5H$_2$O, 0..09 mg/l Na$_2$B$_4$O$_7$.10H$_2$O, 0.04 mg/l (NH$_4$)$_6$Mo$_7$O$_{24}$.4H$_2$O, 30 μg/l biotin and 1 mg/l thiamine hydrochloride are used. Microbial cells are inoculated in the medium and culturing is carried out with shaking. The optical density (OD) of the culture medium at 660 nm is monitored with a colorimeter and penicillin such as penicillin G, is added to the medium at an initial state of the logarithmic growth phase (OD: 0.1–0.4) to a concentration of 0.1 to 2.0 U/ml. Culturing is continued to an OD value of 0.3–0.5, and then cells are harvested and washed with SSM medium. The washed cells are resuspended in a suitable hypertonic medium such as PFM medium (pH 7.0–8.5) wherein 0.4M sucrose and 0.01M $MgCl_2.6H_2O$ are added to 2 fold diluted SSM medium, and RCG medium (pH 7.0–8.5) consisting of 5 g/l glucose, 5 g/l casein hydrolysate, 2.5 g/l yeast extract, 3.5 g/l $K_2HOP_4$, 1.5 g/l $KH_2PO_4$, 0.41 g/l $MgCl_2.6H_2O$, 10 mg/l $FeSO_4.7H_2O$, 2 mg/l $MnSO_4.(4-6)H_2O$, 0.9 mg/l $ZnSO_4.7H_2O$, 0.4 mg/l $CuSO_4.5H_2O$, 0.09 mg/l $Na_2B_4O_7.10H_2O$, 0.04 mg/l $(NH_4)_6Mo_7O_{24}.4H_2O$, 30 μg/l biotin, 2 mg/l thiamine hydrochloride and 135 g/l sodium succinate or RCGP medium which consists of RCG medium and 3% polyvinyl pyrrolidone. To the cell suspension, lysozyme is added to a final concentration of 0.2 to 10 mg/ml, and the mixture is allowed to react at a temperature of 30° to 37° C. Protoplast formation proceeds with time and is monitored under an optical microscope. The period required for the conversion of most cells to protoplasts depends on the concentrations of the penicillin used for the lysozyme-sensitization and the amount of lysozyme used. The period is 3–24 hours under the conditions mentioned above.

Since protoplasts formed are destroyed under hypotonic conditions, the extent of the formation of protoplast is determined indirectly from the number of normal cells surviving under hyptonic conditions. Generally, the ratio of surviving normal cells is kept below $10^{-4}$ per lysozyme-treated normal cell.

The protoplasts prepared as above have colony-forming (regenerating) ability on a suitable hypertonic agar medium. As a regeneration medium, a nutrient medium, a semi-synthetic medium or a synthetic medium containing various amino acids, which contains 0.3 to 0.8M sodium succinate and 0.5 to 6% polyvinyl pyrrolidone with a molecular weight of 10,000 to 40,000 is preferably used. Generally, a semi-synthetic RCGP agar medium (pH 7.2) wherein 3% polyvinyl pyrrolidone (molecular weight of 10,000) and 1.4% agar are added to the RGC medium is used. Regeneration is carried out at a temperature of 25° to 35° C. The cultivation time required for the regeneration of protoplasts depends upon the strain used but usually in 10 to 14 days colonies can be picked up. The efficiency of the regeneration of protoplasts on the RCGP medium also depends on the strain used, the concentrations of the penicillin added during the cultivation and the concentration of lysozyme used. The efficiency is generally $10^{-2}$–$10^{-4}$ cells per normal cell treated with lysozyme.

2. Transformation of the protoplasts with a recombinant DNA.

Introduction of a recombinant DNA into the protoplasts is carried out by mixing the protoplasts and the DNA in a hypertonic solution which protects the protoplasts and by adding to the mixture polyethyleneglycol (PEG, average molecular weight: 1,540–6,000) or polyvinylalcohol (PVA, degree of polymerization: 500–1,500) and a divalent metal cation which stimulates the uptake of DNA. As a stabilizing agent for the hypertonic conditions, those generally used to protect protoplasts of other microorganisms such as sucrose and sodium succinate are also employed. PEG and PVA can be used as a final concentration of 5 to 60% and 1 to 20%, respectively. Divalent metal cations such as $Ca^{++}$, $Mg^{++}$, $Mn^{++}$, $Ba^{++}$ and $Sr^{++}$ are effectively used alone or in combination at a final concentration of 1 to 100 mM. Transformation is carried out at 0° to 25° C.

3. Regeneration of the protoplasts to normal cells and selection of a transformant Regeneration of the protoplasts transformed with a recombinant DNA is carried out in the same way as mentioned above by spreading the protoplasts on a hypertonic agar medium such as RCGP medium containing sodium succinate and polyvinyl pyrrolidone and incubating at a temperature wherein normal cells can grow, generally 25° to 35° C. Transformants are obtained by selecting from the phenotype derived from donor DNAs. The selection may be carried out simultaneously with regeneration on a hypertonic agar medium or may be carried out on a hyptonic agar medium after non-selective reversion to normal cells on a hypertonic agar medium.

In the case of the lysozyme-sensitive strains described as the preferred host microorganisms for cloning, the transformation may be carried out by the steps described in (1) to (3) except the cultured cells are directly treated with lysozyme without prior treatment with penicillin. In that case, transformants are obtained at an efficiency of $10^{-2}$ to $10^{-4}$ per regenerate cell.

The phenotype expression of the recombinant DNA is carried out by growing the transformants in a conventional nutrient medium. Appropriate reagents may be added to the medium according to the phenotypes expected from the genes on the recombinant DNA.

The thus obtained transformant is cultured in a conventional manner used in the production of tryptophan by fermentation. That is, the transformant is cultured in a conventional medium containing carbon sources, nitrogen sources, inorganic materials, amino acids, vitamines, etc. under aerobic conditions, with adjustment of temperature and pH. Thus, tryptophan accumulated in the medium is recovered.

As the carbon source, various carbohydrates such as glucose, fructose, sucrose, maltose, mannose, sorbitol, mannitol, sugar alcohol, glycerol, starch, starch hydrolyzate and molasses, various organic acids such as pyruvic acid, lactic acid, acetic acid, fumaric acid and gluconic acid, and lower alcohols such as ethanol may be used.

As the nitrogen source, ammonia, various inorganic or organic ammonium salts such as ammonium chloride, ammonium sulfate, ammonium carbonate and ammonium acetate, urea, and nitrogenous organic substances such as peptone, NZ-amine, meat extract, yeast textract, corn steep liquor, casein hydrolyzate, fish meal or its digested product, and chrysalis hydrolyzate are appropriate.

As the inorganic materials, potassium dihydrogenphosphate, dipotassium hydrgenphosphate, magnesium sulfate, sodium chloride, ferrous sulfate, manganese sulfate and calcium carbonate may be used. Vitamines and amino acids required for the growth of microorganisms may not be added, provided that they are supplied with other components mentioned above.

Culturing is carried out under aerobic conditions with shaking or aeration-agitation. Culturing temperature is preferably 20° to 40° C. The pH of the medium during culturing is maintained around neutral. Culturing is continued until a considerable amount of tryptophan is accumulated, generally for 2 to 5 days.

After completion of the culturing, cells are removed and tryptophan is recovered from the culture liquor by conventional manners such as treatment with active carbon or ion exchange resin.

In spite of the high similarility in microbiological characteristics, so called glutamic acid-producing microorganisms which product glutamic acid in large amounts are classified into various species and even into different genera such as Corynebacterium and Brevibacterium, which is probably because of their industrial importance. However, it has been pointed out that these microorganisms should belong to one species because of nearly the same composition of amino acids in the cell wall and the base completion of DNAs. Recently, it has been reported that these microorganisms have 70 to 80% or more homology in DNA indicating that these micoorganisms are closely related. See, e.g., Komatsu, Y.: Report of the Fermentation Research Institute, No. 55, 1 (1980), and Suzuki, K., Kaneko, T., and Komagata, K.: Int. J. Syst. Bacteriol., 31, 131 (1981).

In the present specification, the usefulness of the present invention is illustrated using derivatives of *Corynebacterium glutamicum* L-22 as host microorganisms because of the restrictions on experiments of recombinant DNA technology in Japan. However, in consideration of the facts mentioned above, it is apparent that the usefulness of the present invention is applicable to all the glutamic acid-producing microorganisms. In order to stably maintain recombinant DNA molecules and express the DNA in these species, slight differences in such properties of the host microorganisms as homology in the DNA are negligible and it is sufficient for host microorganisms to allow the autonomous replication of plasmids and expression of genes on them. That these microorganisms have such abilities is apparent from the fact that plasmid pCG4 which was isolated from *Corynebacterium glutamicum* 225-250 and having an $Sm^R/Spec^R$ gene (Japanese Published Unexamined Patent Application No. 183799/82) could replicate in microorganisms belonging to the genus Corynebacterium or Brevibacterium and the gene responsible for the resistance could be expressed (Japanese Published Unexamined Patent Application No. 186492/82). Therefore, the present invention is applicable to all the glutamic acid-producing microorganisms including those microorganisms belonging to the genus Corynebacterium or Brevibacterium as well as to *Cornynebacterium glutamicum*.

Certain specific embodiments of the present invention are illustrated by the following representative examples.

EXAMPLE 1

Cloning of the anthranilic acid synthetase gene of Brevibacterium flavum ATCC 14067 and production of tryptophan in *Corynebacterium glutamicum*

(1) Preparation of chromosomal DNA and plasmid pCE53

The chromosomal DNA of *Brevibacterium flavum* ATCC 14067 was prepared as follows:

A seed culture in NB medium was inoculated into 400 ml of semi-synthetic medium SSM (pH 7.2) consisting of 20 g/l glucose, 10 g/l $(NH_4)_2SO_4$, 3 g/l urea, 1 g/l yeast extract, 1 g/l $KH_2PO_4$, 0.4 g/l $MgCl_2.6H_2O$, 10 mg/l $FeSO_4.7H_2O$, 0.2 mg/l $MnSO_4.(4-6)H_2O$, 0.9 mg/l $ZnSO_4.7H_2O$, 0.4 mg/l $CuSO_4.5H_2O$, 0.09 mg/l $Na_2B_4O_7.10H_2O$, 0.04 mg/l $(NH_4)_6Mo_7O_{24}.4H_2O$, 30 μg/l biotin and 1 mg/l thiamine hydrochloride. Culturing was carried out with shaking at 30° C. The optical density (OD) at 660 nm was monitored with a Tokyo Koden colorimeter and penicillin G was added at an OD value of 0.2 to a concentration of 0.5 unit/ml. Culturing was continued to an OD value of about 0.6.

Cells were harvested from the culture broth and washed with TES buffer (pH 8.0) consisting of 0.3M tris(hydroxymethyl) aminomethane-HCl (referred to as Tris hereinafter), 0.005M EDTA and 0.05M NaCl. The cells were suspended in a lysozyme solution (pH 8.0) consisting of 25% sucrose, 0.1M NaCl, 0.05M Tris and 0.8 mg/ml lysozyme to make 10 ml of a suspension which was allowed to react at 37° C. for 4 hours. High molecular chromosomal DNAs were isolated from the cells by the method of Saito et al., Biochim. Biophys. Acta, 72, 619 (1963). pCE53 used as a vector plasmid was isolated from *Corynebacterium glutamicum* L-22 having pCE53 as follows.

The strain was grown with shaking at 30° C. in 400 ml of NB medium (pH 7.2) to an OD value of about 0.7. Cells were harvested and washed with TES buffer. The cells were suspended in 10 ml of the aforementioned lysozyme solution and allowed to react at 37° C. for 2 hours. Then 2.4 ml of 5M NaCl, 0.6 ml of 0.5M EDTA (pH 8.5) and 4.4 ml of a solution consisting of 4% sodium lauryl sulfate and 0.7M NaCl were added successively. The mixture was stirred slowly and allowed to stand in an ice water bath for 15 hours. The whole lysate was centrifuged at 4° C. at 69,400×g for 60 minutes. The supernatant fluid was recovered and 10% (by weight) polyethyleneglycol (PEG) 6,000 (product of Nakarai Kagaku Yakuhin Co.) was added. The mixture was stirred slowly to dissolve completely and then kept in an ice water bath. After 10 hours, the mixture was centrifuged at 1,500×g for 10 minuts to recover a pellet. After the pellet was redissolved gently in 5 ml of TES buffer, 2.0 ml of 1.5 mg/ml ethidium bromide was aded. Then, cesium chloride was added to adjust the density of the mixture to 1,580. The solution was centrifuged at 18° C. at 105,000×g for 48 hours. After the density gradient centrifugation, a covalently-closed circular DNA was detected under UV irradiation as a high density band located in the lower part of the centrifugation tube. The band was taken out from the side of the tube with an injector to obtain a fraction containing pCG11 DNA. To remove ethidium bromide, the fraction was treated five times with an equal amount of cesium chloride saturated isopropyl alcohol solution consisting of 90% by volume isopropyl alcohol and 10% TES buffer solution. Then, the residue was dialysed against TES buffer solution.

Plasmid pCE53 is a recombinant plasmid wherein plasmid pCG1 (Japanese Published Unexamined Patent Application No. 134500/82) of *Corynebacterium glutamicum* is combined with plasmid pGA22 of *Escherichia coli* described by An, G. et al., J. Bacteriol 140, 400 (1979). More specifically, pCE53 was constructed by inserting BglII restricted pCG1 into the BamHI site near the $Km^R$ gene of pGA22 and ligating by taking advantage of the same cohesive ends formed by both restriction enzymes. pCE53 has selective markers such as $Km^R$ derived from pGA22 and has only one cleavage site for SalI.

(2) Cloning of the anthranilic acid synthetase gene:

10 units of restriction enzyme SalI (product of Takara Shuzo Co.) was added to 200 μl of the SalI reaction solution containing 3 μg of pCE53 plasmid DNA prepared as above and 9 μg of the chromosomal DNA. The mixture was allowed to react to 37° C. for 60 minutes and heated at 65° C. for 10 minutes to stop the reaction. Then, 40 μl of the T4 ligase buffer (pH 7.6) consisting of 660 mM Tris, 66 mM $MgCl_2$ and 100 mM dithiothreitol, 40 μl of 5 mM ATP, 0.4 μl of T4 ligase (product of Takara Shuzo Co., 1 unit/μl) and 120 μl of $H_2O$ were added to the digest. The mixture was allowed to react at 12° C. for 16 hours.

(3) Transformation with the recombinant plasmid:

The ligation mixture was used to transform strain LA 105, which is a mutant requiring anthranilic acid due to the lack of the anthranilic acid synthetase gene and derived from *Corynebacterium glutamicum* L-22. The mutant was obtained by a conventional mutagenesis as a strain which could not grow on M1 agar medium (pH 7.2) consisting of 10 g/l glucose, 1 g/l $NH_4H_2PO_4$, 0.2 g/l KCl, 0.2 g/l $MgSO_4.7H_2O$, 10 mg/l $FeSO_4.7H_2O$, 0.2 mg/l $MnSO_4.(4-6)H_2O$, 0.9 mg/l $ZnSO_4.7H_2O$, 0.4 mg/l $CuSO_4.5H_2O$, 0.90 mg/l $Na_2B_4O_7.10H_2O$, 0.04 mg/l $(NH_4)_6Mo_7O_{24}.4H_2O$, 50 μg/l biotin, 2.5 mg/l p-aminobenzoic acid, 1 mg/l thamine hydrochloride and 16 g/l agar and could grown on M1 agar medium containing 30 μg/ml anthranilic acid. Preparation of the protoplasts of LA 105 and transformation of the protoplasts were carried out using LA 105 cells grown on NB medium containing 100 μg/ml anthranilic acid as follows.

The seed culture of LA 105 strain was inoculated into NB medium and culturing was carried out with shaking at 30° C. Cells were harvested at an OD value of 0.6. The cells were suspended at about $10^9$ cells/ml in RCGP medium (pH 7.6) consisting of 5 g/l glucose, 5 g/l casamino acid, 2.5 g/l yeast extract, 3.5 g/l $K_2HPO_4$, 1.5 g/l $KH_2PO_4$, 0.41 g/l $MgCl_2.6H_2O$, 10 mg/l $FeSO_4.7H_2O$, 2 mg/l $MnSO_4.(4-6) H_2O$, 0.9 mg/l $ZnSO_4.7H_2O$, 0.04 mg/l $(NH_4)_6Mo_7O_{24}.4H_2O$, 30 μg/l biotin, 2 mg/l thamine hydrochloride, 135 g/l sodium succinate and 30 g/l polyvinyl pyrrolidone with a molecular weight of 10,000 and containing 1 mg/ml lysozyme. The suspension was put in an L-tube and shaken slowly at 30° C. for 5 hours to obtain protoplasts.

Then, 0.5 ml of the protoplast suspension was put in a small test tube and centrifuged at 2,500×g for 5 minutes. The protoplasts were resuspended in 1 ml of TSMC buffer (pH 7.5) consisting of 10 mM magnesium chloride, 30 mM calcium chloride, 50 mM Tris and 400 mM sucrose and again subjected to centrifugation and washing. The washed protoplasts were resuspended in 0.1 ml of TSMC buffer solution. 100 μl of a mixture (1:1 by volume) of two-fold concentrated TSMC buffer solution and the ligated DNA mixture described above was added to the protoplast suspension. Then, 0.8 ml of TSMC buffer containing 20% PEG 6,000 was added to the mixture. After 3 minutes, 2 ml of RCGP medium (pH 7.2) as added and the mixture was centrifuged at 2,500×g for 5 minutes. The supernatant fluid was removed and the protoplasts were suspended in 1 ml of RCGP medium. Then, 0.2 ml of the suspension was spread on RCGP agar medium (pH 7.2) containing 300 μg/ml kanamycin and 1.4% agar and incubated at 30° C. for 7 days.

Colonies resistant to kanamycin grown on the selection plate were scraped, washed with physiological saline solution and centrifuged two times. The cells were spread on M1 minimal agar medium containing 20 μg/ml kanamycin and incubated at 30° C. for 2 days. Transformants which were resistant to kanamycin and did not require anthranilic acid were selected.

Plasmid DNAs were isolated from the cells of these transformants in the same way as mentioned above. The plasmid pTrp 2-3, recovered from one of the transformants, were analyzed by digestion with various restriction endonucleases and agarose gel electrophoresis. As a result, the plasmid pTRp 2-3 was found to contain an about 7.1 Kb SalI DNA fragment inserted into the unique SalI site of pCE53.

Strain LA 105 was retransformed with pTrp 2-3 in the same way as mentioned above. The colonies grown on RCGP agar medium containing 100 μg/ml tryptophan and 400 μg/ml kanamycin did not require anthranilic acid for growth and they had the same plasmid as pTrp 2-3 characterized by the cleavage pattern by SalI.

The result shows that the gene coding for anthranilic acid synthetase of *Brevibacterium flavum* ATCC 14067 is present in the cloned SalI DNA fragment of about 7.1 Kb and expressed in *Corynebacterium glutamicum* LA 105.

A microorganism containing pTrp 2-3, *Corynebacterium glutamicum* K-20, has been deposited with the American Type Culture Collection, U.S.A. under accession number ATCC 39035.

(4) Production of tryptophan by a transformant

Plasmid pTrp 4-3 carrying the anthranilic acid synthetase gene of *Brevibacterium flavum* ATCC 14067 was obtained using plasmid pCE52 by the same method as mentioned above.

Plasmid pCE52 is a recombinant plasmid wherein plasmid pCG1 (Japanese Published Unexamined Patent Application No. 134500/82) of *Corynebacterium glutamicum* is combined with plasmid pGA22 of *Escherichia coli* described by An, G. et al., J. Bacteriol 140, 400 (1979). It was constructed by inserting BglII restricted pCg1 into the BamHI site in the $Tc^R$ gene of pGA22 and ligating by taking advantage of the same cohesive ends formed by both restriction enzymes. pCE52 has selective markers such as $Km^R$ derived from pGA22 and has only one cleavage site for SalI.

pCE52 was isolated from the cells of *Corynebacterium glutamicum* L-22 containing pCE52 as follows:

The strain was grown with shaking at 30° C. in 400 ml of NB medium (pH 7.2) to an OD value of about 0.7. Cells were harvested and washed with TES buffer. The cells were suspended in 10 ml of aforementioned lysozyme solution and allowed to react at 37° C. for 2 hours. Then 2.4 ml of 5M NaCl, 0.6 ml of 0.5M EDTA (pH 8.5) and 4.4 ml of a solution consisting of 4% sodium lauryl sulfate and 0.7M NaCl were added successively. The mixture was stirred slowly and allowed to stand in an ice water bath for 15 hours. The whole lysate was centrifuged at 4° C. at 69,400×g for 60 minutes. The supernatant fluid was recovered and 10% (by weight) polyethyleneglycol (PEG) 6,000 (product of Nakarai Kagaku Yakuhin Co.) was added. The mixture was stirred slowly to dissolved completely and then kept in an ice water bath. After 10 hours, the mixture was centrifuged at 1,500×g for 10 minutes to recover a pellet. After the pellet was redissolved gently in 5 ml of TES buffer, 2.0 ml of 1.5 mg/ml ethidium bromide was added. Then, cesium-chloride was added to adjust the density of the mixture to 1.580. The solution was centrifuged at 18° C. at 105,000×g for 48 hours. After the density gradient centrifugation, a covalently-closed circular DNA was detected under UV irradiation as a high density band located in the lower part of the centrifugation tube. The band was taken out from the side of the tube with an injector to obtain a fraction containing pCG11 DNA. To remove ethidium bromide, the fraction was treated five times with an equal amount of cesium chloride saturated isopropyl alcohol solution consisting of 90% by volume isopropyl alcohol and 10% TES buffer solution. Then, the residue was dialysed against TES buffer solution.

Tryptophan-producing *Cornyebacterium glutamicum* LAR-1 (FERM P-6908) was transformed wtih pTrp 4-3 as mentioned above. The thus obtained transformant has been deposited with the American Type Culture Collection as *Cornyebacterium glutamicum* K31, ATCC 39280.

*Corynebacterium glutamicum* K20, ATCC 39035 containing pTrp 2-3 and K31, ATCC 39280 containing pTrp 4-3 were tested for production of L-tryptophan as follows:

These strains were cultured with shaking at 30° C. in NB medium for 16 hours and 0.5 ml of the cultured broth was inoculated in 5 ml of the production medium P4 (pH 7.2) consisting of 100 g/l molasses, 20 g/l $(NH_4)_2SO_4$, 0.5 g/l $KH_2PO_4$, 0.5 g/l $K_2HPO_4$, 0.25 g/l $MgSO_4.7H_2O$ and 20 g/l $CaCO_3$. Culturing was carried out with shaking at 30° C. for 96 hours.

After culturing, the culture filtrate was subjected to paper chromatography. After ninhydrin color reaction, the amount of L-tryptophan produced was determined by a colorimetric method.

As control strains, LA-105 and LAR-1 were subjected to similar treatment. The results are shown in Table 1.

TABLE 1

| Strain | Amount of L-tryptophan (mg/ml) |
|---|---|
| LA-105 | — |
| LA-105/pTrp2-3 (K20, ATCC 39035) | 0.34 |
| LAR-1 | 0.48 |
| LAR-1/pTrp4-3 (K31, ATCC 39280) | 1.12 |

EXAMPLE 2

Cloning of the anthranilic acid synthetase gene of *Corynebacterium glutamicum* ATCC 13032 and production of tryptophan in *Corynebacterium glutamicum*:

(1) Preparation of the chromosomal DNA

The chromosomal DNA of *Corynebacterium glutamicum* ATCC 13032 was prepared by the following method.

The chromosomal DNA was prepared by the same methods as in Example 1(1) except that *Corynebacterium glutamicum* ATCC 13032 was used in place of *Brevibacterium flavum* ATCC 14067.

(2) Cloning of the anthranilic acid synthetase gene

A ligation mixture was obtained by the same method as in Example 1(2) using 3 μg of pCE52 plasmid DNA prepared in Example 1(4) and 9 μg of the chromosomal DNA prepared above.

(3) Transformation of the recombinant plasmid

Transformants were obtained by the same method as in Example 1(3) using the ligation mixture prepared above.

Plasmid DNAs were isolated from the cultured cells of these transformants in the same way as mentioned above. The plasmid pTrp 9-1, recovered from one of the transformants, was analyzed by digestion with various restriction enconucleases and agarose gel electrophoresis. As a result, the plasmid pTrp 9-1 was found to contain a SalI DNA fragment of about 7.3 Kb inserted into the unique SalI site of pCE52.

Strain LA 105 was retransformed with pTrp 9-1 in the same way as mentioned above. The colonies grown on RCGP agar medium containing 100 μg/ml tryptophan and 400 μg/ml kanamycin did not require anthranilic acid for growth and they had the same plasmid as pTrp 9-1 characterized by the cleavage pattern by SalI.

The result shows that the gene coding for anthranilic acid synthetase of *Corynebacterium glutamicum* ATCC 13032 is present in the cloned SalI DNA fragment of about 7.3 Kb and expressed in *Corynebacterium glutamicum* LA 105.

(4) Recovering of plasmid pTrp 13-2 resistant to a tryptophan analog from a strain containing pTrp 9-1

LA-10 strain containing pTrp 9-1 was grown in NB medium containing 10 μg/ml kanamycin to a late stage of the logarithmic growth phase. Cells were recovered by centrifugation and washed with 50 mM Tris-malate buffer (pH 6.0) two times. The washed cells were incubated at room temperature in 50 mM Tris-malate buffer (pH 6.0) containing 400 μg/ml N-methyl-N'-nitro-N-nitrosoguanidine for 30 minutes. The treated cells were washed with 50 mM Tris-malate buffer (pH 6.0) and centrifuged two times. The washed cells were cultured at 30° C. in NB medium containing 10 μg/ml kanamycin for 16 hours. Plasmid DNAs were isolated by the same method as in Example 1.

LA-105 strain was transformed using the isolated plasmid DNAs by the same method as in Example 1. Selection of transformants were carried out on RCGP agar medium containing 0.5 mg/ml 4-methyltryptophan or 0.5 mg/ml 6-fluorotryptophan, with or without 200 μg/ml kanamycin.

Colonies grown on M1 agar medium containing 0.5 mg/ml of the corresponding tryptophan analog and on NB agar medium containing 10 μg/ml kanamycin were selected.

The thus obtained transformants have the plasmid harboring a gene coding for the anthranilic acid synthetase insensitie to tryptophan. The anthranilic acid synthetase encoded by one of the plasmids, pTrp 13-2 was inhibited 50% with 0.25 mM tryptophan, which was 40-fold higher than the concentration of tryptophan (0.006 mM) needed to inhibit 50% the anthranilic acid synthetase encoded by pTrp 9-1.

*Corynebacterium glutamicum* LAR-1 was transformed with pTrp 13-2 by the same method as in Example 1. The thus obtained transformant has been deposited with the American Type Culture Collection as *Corynebacterium glutamicum* K37, ATCC 39285.

(5) Production of tryptophan by the transformant:

*Corynebacterium glutamicum* K37, ATCC 39285 containing pTrp 13-2 was tested for production of tryptophan as follows:

The strain was cultured with shaking at 30° C. in NB medium for 16 hours and 0.5 ml of the cultured broth was inoculated in 5 ml of the production medium P4 (pH 7.2) consisting of 100 g/l molasses, 20 g/l $(NH_4)_2SO_4$, 0.5 g/l $KH_2PO_4$, 0.5 g/l $K_2HPO_4$, 0.25 g/l $MgSO_4.7H_2O$, and 20 g/l $CaCO_3$. Culturing was carried out with shaking at 30° C. for 96 hours.

After culturing, the culture filtrate was subjected to paper chromatography. After ninhydrin color reaction, the amount of L-tryptophan produced was determined by a colorimetric method.

LAR-1 strain and LAR-1/pTrp 9-1 strain were used as control strains. LAR-1/pTrp 9-1 was prepared by the same transformation of LAR-1 strain as mentioned above. The results are shown in Table 2.

TABLE 2

| Strain | Amount of L-tryptophan (mg/ml) |
|---|---|
| LAR-1 | 0.4 |
| LAR-1/pTrp 9-1 | 0.7 |
| LAR-1/pTrp 13-2 | 1.2 |

What is claimed is:

1. A process for producing tryptophan, which comprises:
   transforming a host microorganism belonging to the genus Corynebacterium or Brevibacterium with a vector containing a DNA fragment containing an anthranilic acid synthetase gene isolated from Brevibacterium flavum ATCC 14067 or Corynebacterium glutamicum ATCC 13032, culturing the transformant in a nutrient medium containing a molasses carbon source, accumulating tryptophan in the culture medium and recovering tryptophan therefrom.

2. The process according to claim 1, wherein the host microorganism belongs to the genus Corynebcterium or Brevibacterium and is sensitive to lysozyme.

3. A process for producing tryptophan, which comprises:
   culturing in a nutrient medium containing a molasses carbon source a microorganism belonging to the genus Corynebacterium or Brevibacterium comprising a vector containing a DNA fragment encoding an anthranilic acid synthetase insensitive to tryptophan, which fragment was isolated fom Brevibacterium flavum ATCC 14067 or *Corynebacterium glutamicum* ATCC 13032, accumulating tryptophan in the culture medium and recovering tryptophan therefrom.

4. A microorganism belonging to the genus Corynebacterium or Brevibacterium and comprising a vector containing a DNA fragment encoding an anthranilic acid synthetase insensitive to tryptophan, which fragment was isolated from Brevibacterium flavum ATCC 14067 or *Corynebacterium glutamicum* ATCC 13032.

5. A micoorganism belonging to the genus Corynebacterium or Brevibacterium comprising vector containing a DNA fragment containing an anthranilic acid synthetase gene isolated from Brevibacterium flavum ATCC 14067 or *Corynebacterium glutamicum* ATCC 13032.

6. A biologically pure culture of *Corynebacterium glutamicum* K20, ATCC 39035, which contains plasmid pTrp 2-3.

7. A biologically pure culture of *Corynebacterium glutamicum* K31, ATCC 39280, which contains plasmid pTrp 4-3.

8. A biologically pure culture of *Corynebacterium glutamicum* K37, ATCC 39285, which contains plasmid pTrp 13-2.

* * * * *

UNITED STATES PATENT AND TRADEMARK OFFICE
CERTIFICATE OF CORRECTION

PATENT NO. : 4,874,698
DATED : October 17, 1989
INVENTOR(S) : AKIO OZAKI ET AL.

Page 1 of 4

It is certified that error appears in the above-identified patent and that said Letters Patent is hereby corrected as shown below: ON TITLE PAGE:

AT [56] REFERENCES CITED

Foreign Patent Documents, "0553843 of 0000 Australia" should read --0553843 8/1982 Australia--; "0556761 6/1983 Australia" should read --0556761 12/1982 Australia-- and

COLUMN 1

Line 35, "Unexampined" should read --Unexamined--.

COLUMN 2

Line 19, "sile" should read --sible--.
Line 28, "Unexemined" should read --Unexamined--.
Line 47, "foregong" should read --foregoing--.

COLUMN 4

Line 32, "transformant;" should read --transformant.--.
Line 51, "with" should read --and--.

COLUMN 5

Line 5, "$K_2HOP_4$," should read --$K_2HPO_4$,--.
Line 62, "as" should read --at--.

UNITED STATES PATENT AND TRADEMARK OFFICE
CERTIFICATE OF CORRECTION

PATENT NO. : 4,874,698

DATED : October 17, 1989

INVENTOR(S) : AKIO OZAKI ET AL.

Page 2 of 4

It is certified that error appears in the above-identified patent and that said Letters Patent is hereby corrected as shown below:

COLUMN 6

Line 14, "hyptonic" should read --hypotonic--.
    Line 20, "except the" should read --except that the--.
    Line 23, "regenerate" should read --regenerated--.
    Line 24, "phenotype" shoudl read --phenotypic--.
    Line 48, "yeast textract," should read --yeast extract,--.
    Line 53, "hydrgenphosphate," should read --hydrogenphosphate--.

COLUMN 7

Line 1, "similarility" should read --similarity--.
    Line 2, "so called" should read --so-called--.
    Line 59, "of semi-synthetic" should read --of a semi-synthetic--.

COLUMN 8

Line 32, "10 minuts" should read --10 minutes--.
    Line 35, "aded." should read --added.--.
    Line 67, "react to" should read --react at--.

COLUMN 9

Line 18, "0.90 mg/l $Na_2B_4O_7.10H_2O$," should read --0.09 mg/l $Na_2B_4O_7.10H_2O$,--.
    Line 20, "thamine" should read --thiamine--.
    Line 36, "thamine" should read --thiamine--.
    Line 55, "as" should read --was--.

UNITED STATES PATENT AND TRADEMARK OFFICE
CERTIFICATE OF CORRECTION

PATENT NO. : 4,874,698
DATED : October 17, 1989
INVENTOR(S) : AKIO OZAKI ET AL.

Page 3 of 4

It is certified that error appears in the above-identified patent and that said Letters Patent is hereby corrected as shown below:

COLUMN 10

Line 4, "were" should read --was--.
Line 6, "plasmid pTRp 2-3" should read --plasmid pTrp 2-3--.
Line 36, "pCgl" should read --pCG1--.
Line 46, "aforementined" should read --aforementioned--.
Line 57, "dissolved" should read --dissolve--.

COLUMN 11

Line 9, "wtih" should read --with--.
Line 51, "methods" should read --method--.

COLUMN 12

Line 1, "enconucleases" should read --endonucleases--.
Line 19, "LA-10 strain" should read --LA-105 strain--.
Line 35, "were" should read --was--.
Line 45, "insensitie" shoud read --insensitive--.

COLUMN 13

Line 33, "Corynebcterium" should read --Corynebacterium--.

UNITED STATES PATENT AND TRADEMARK OFFICE
CERTIFICATE OF CORRECTION

PATENT NO. : 4,874,698

DATED : October 17, 1989

INVENTOR(S) : AKIO OZAKI ET AL.

Page 4 of 4

It is certified that error appears in the above-identified patent and that said Letters Patent is hereby corrected as shown below:

COLUMN 14

Line 8, "fom" should read --from--.
Line 20, "comprising vector" should read --comprising a vector--.

Signed and Sealed this

Twenty-eighth Day of April, 1992

Attest:

HARRY F. MANBECK, JR.

Attesting Officer

Commissioner of Patents and Trademarks